(12) United States Patent
Nagy et al.

(10) Patent No.: US 7,152,454 B2
(45) Date of Patent: Dec. 26, 2006

(54) CONTINUOUS BLENDING FOR GAS ANALYZER CALIBRATION

(75) Inventors: Donald B. Nagy, Canton, MI (US); Steven S. De Carteret, Beverly Hills, MI (US)

(73) Assignee: General Motors Corporation, Detroit, MI (US)

( * ) Notice: Subject to any disclaimer, the term of this patent is extended or adjusted under 35 U.S.C. 154(b) by 175 days.

(21) Appl. No.: 10/662,834

(22) Filed: Sep. 15, 2003

(65) Prior Publication Data

US 2005/0056079 A1 Mar. 17, 2005

(51) Int. Cl.
*G01N 35/00* (2006.01)
(52) U.S. Cl. ....................................... 73/1.06
(58) Field of Classification Search ................ 73/1.06, 73/1.07, 23.21, 23.31
See application file for complete search history.

(56) References Cited

U.S. PATENT DOCUMENTS 3,924,442 A * 12/1975 Kerho et al. ............... 73/23.21

5,835,974 A 11/1998 Nagy

OTHER PUBLICATIONS

C.D. Paulsell, P.E., "The Use Of Exponential Dilution Flow in Gas Analyzer Calibrations", U.S. Environmental Protection Agency, Ann Arbor, MI 48105.

* cited by examiner

Primary Examiner—Hezron Williams
Assistant Examiner—Paul M. West
(74) Attorney, Agent, or Firm—Christopher DeVries

(57) ABSTRACT

A method for calibrating a plurality of gas analyzers includes providing gas analyzers that measure the concentrations of gases. A span gas includes a mixture of the gases. A calibration mixture is supplied to the gas analyzers that includes the span gas and a non-reactive zero gas. At least one of a concentration of the non-reactive zero gas and a concentration of the span gas is varied in the calibration mixture as a function of time. The gas analyzers generate sets of readings of the concentrations of the gases. A controller generates response functions of the gas analyzers based on the sets of readings. The controller determines exact concentrations of the gases in the calibration mixture based on a set of readings from a gas analyzer with a predetermined response to a gas. The controller calibrates the gas analyzers based on the response functions and the exact concentrations.

20 Claims, 4 Drawing Sheets

CONTINUOUS BLENDING FOR GAS ANALYZER CALIBRATION

FIELD OF THE INVENTION

The present invention relates to gaseous emissions testing, and more particularly to the calibration and diagnosis of gas analyzers used in gaseous emissions testing.

BACKGROUND OF THE INVENTION

Gaseous emissions testing may include the testing of stack gas, stationary sources, mobile sources, ambient air modeling, or vehicle sources (such as engines or other power plants). For example, test sites for engine exhaust gas emission testing generally include one or more test benches. Each test bench includes multiple exhaust gas analyzers that determine concentrations of different gases in a sample of engine exhaust, which may be diluted or undiluted. The exhaust gas analyzers are periodically calibrated to ensure that the collected data is accurate.

The exhaust gas analyzers are connected to a source of non-reactive zero gas and a separate span gas for each exhaust gas analyzer range to be tested. The span gas supplies have a predetermined concentration of a particular gas, which the corresponding exhaust gas analyzer senses. A base reading is obtained from the exhaust gas analyzers by supplying only the zero gas. Intermediate readings are obtained for each exhaust gas analyzer by mixing the corresponding span gas and the zero gas and by supplying the mixture to the exhaust gas analyzer. Multiple tests are performed on each exhaust gas analyzer by varying the concentration of the span gas in the mixture. The process is repeated for the other exhaust gas analyzers on the test bench.

In one method, a gas divider dilutes the span gas using the zero gas to a first divide point. The divided gas is routed to the exhaust gas analyzer for a reading. The procedure is repeated for a discrete number of divide points. For example, ten divide points may be used. The process is performed for each of the exhaust gas analyzers on the test bench. The gathered data is used to create a best fit equation for each exhaust gas analyzer. The equations are programmed into a computer to calibrate the exhaust gas analyzers. The calibration process is time consuming and expensive due to the time required to allow the divisions of zero gas and span gas to stabilize. Additionally, extensive plumbing and control equipment is required.

Another method involves supplying a single blended span gas that includes all of the gases to which the exhaust gas analyzers on a test bench are responsive. The blended span gas is diluted with a zero gas and discrete divisions, for example 10 divisions, are supplied to all of the exhaust gas analyzers simultaneously for readings. The process is repeated for each exhaust gas analyzer range. When different exhaust gas analyzer ranges are used, drifting in the exhaust gas analyzers causes measurement errors. A discrete number of divisions of span gas and zero gas does not accurately describe an exhaust gas analyzer curve. Also, hysteresis in exhaust gas analyzers causes measurement errors.

Commercially available dividers can provide as many as 1000 divisions of span gas and zero gas. However, these dividers are very expensive. The amount of time that is required between divisions to allow the exhaust gas analyzer readings to stabilize is large.

SUMMARY OF THE INVENTION

A method for calibrating a plurality of gas analyzers according to the present invention includes providing a first gas analyzer that measures a first concentration of a first gas. A second gas analyzer measures a second concentration of a second gas. A span gas includes a mixture of the first gas and the second gas. A calibration mixture is supplied to both the first gas analyzer and the second gas analyzer. The calibration mixture includes the span gas and a non-reactive zero gas. At least one of a third concentration of the non-reactive zero gas and a fourth concentration of the span gas is varied in the calibration mixture as a function of time.

In other features, at least one of the third concentration and the fourth concentration is varied as a linear function of time. The first gas analyzer generates a first set of readings of the first concentration and the second gas analyzer generates a second set of readings of the second concentration. A controller generates a first response function of the first gas analyzer based on the first set of readings and the controller generates a second response function of the second gas analyzer based on the second set of readings. The first gas analyzer has a predetermined response to the first gas and the controller determines an exact concentration of the second gas in the calibration mixture based on the first set of readings. The predetermined response is determined through precalibration of the first gas analyzer. The predetermined response is linear. The first gas analyzer is a flame ionization detector that measures HC.

In still other features of the invention, the controller calibrates the second gas analyzer based on the second response function and the exact concentration. The controller diagnoses a defect in the second gas analyzer based on the second response function and the exact concentration. A time delay in acquiring at least one reading is mathematically compensating for in the first set of readings and the second set of readings. The first gas and the second gas are selected from the group consisting of hydrocarbons (HC), nitrogen oxides ($NO_x$), carbon monoxide (CO), and carbon dioxide ($CO_2$).

In yet other features, the third concentration is increased as a function of time to generate a first decreasing set of readings of the first concentration and a second decreasing set of readings of the second concentration. The third concentration is decreased as a function of time to generate a first increasing set of readings of the first concentration and a second increasing set of readings of the second concentration. A controller generates a first response function of the first gas analyzer based on a composite of the first decreasing set of readings and the first increasing set of readings, and the controller generates a second response function of the second gas analyzer based on a composite of the second decreasing set of readings and the second increasing set of readings. The calibration mixture is blended in a mixing chamber. A portable device that includes the first gas, the second gas, the zero gas, and a mixing chamber supplies the calibration mixture.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
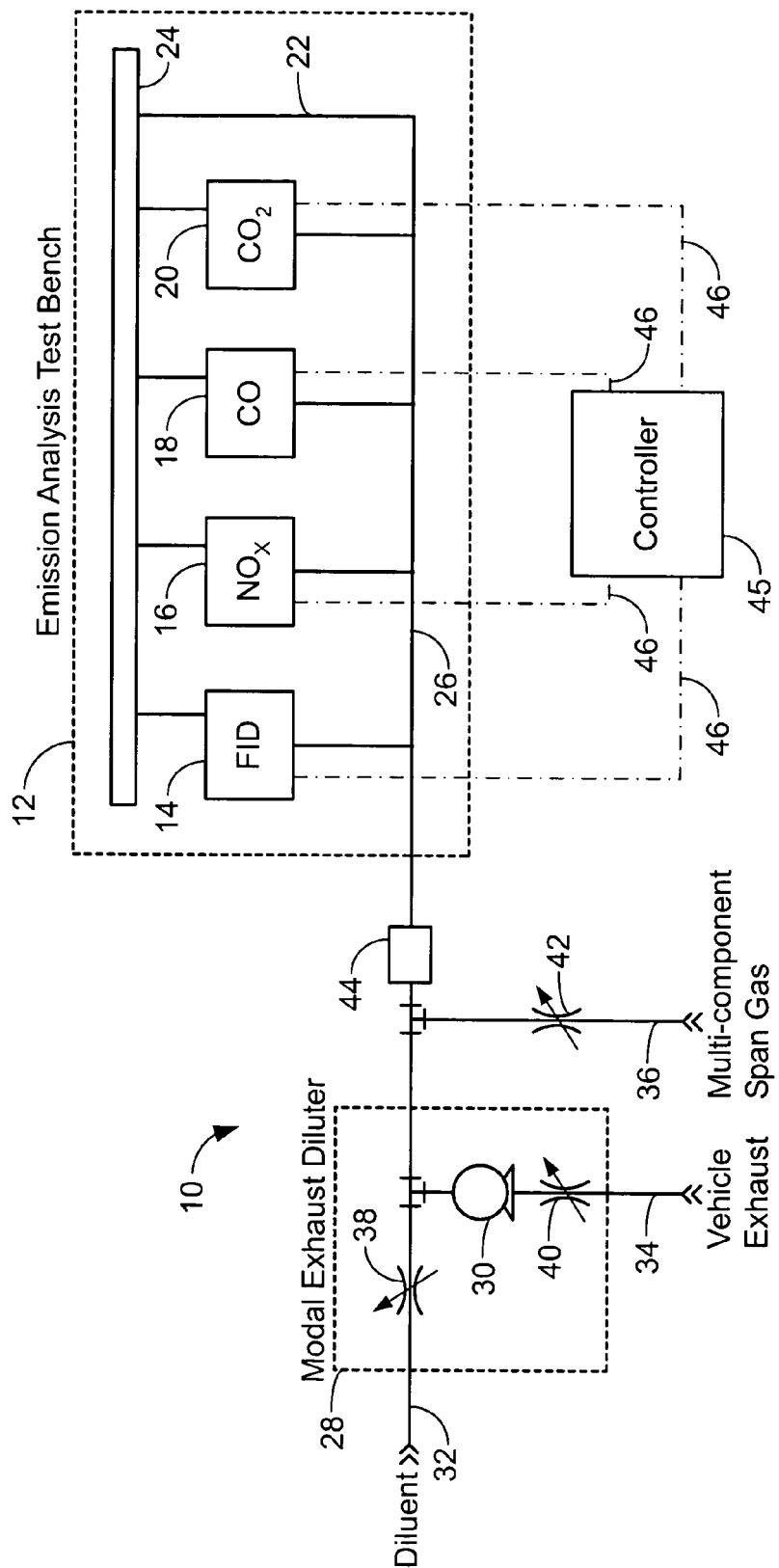
FIG. 1 is a schematic of an emission analysis test bench including a multi-component span gas supply line for exhaust gas analyzer calibration.

The following description of the preferred embodiment(s) is merely exemplary in nature and is in no way intended to limit the invention, its application, or uses. For purposes of clarity, the same reference numbers will be used in the drawings to identify similar elements.

Referring to FIG. 1, a gas flow system 10 is shown that supplies vehicle exhaust gas to an emission analysis test bench 12. The present invention could also be used for bag, engine out, and intermediate types of emission analysis test benches. The emission analysis test bench 12 includes a flame ionization detector (FID) analyzer 14, a nitrogen oxide ($NO_X$) analyzer 16, a carbon monoxide (CO) analyzer 18, and a carbon dioxide ($CO_2$) analyzer 20. The FID analyzer 14 measures the concentration of hydrocarbons (HC) in a sample of vehicle exhaust supplied to the gas flow system 10. Likewise, the $NO_X$ analyzer 16 measures the concentration of nitrogen oxides, the CO analyzer 18 measures the concentration of carbon monoxide, and the $CO_2$ analyzer 20 measures the concentration of carbon dioxide in a vehicle exhaust sample. The FID analyzer 14, $NO_X$ analyzer 16, CO analyzer 18, $CO_2$ analyzer 20, and an exhaust gas analyzer bypass line 22 are connected between an exhaust manifold 24 and a supply manifold 26.

A diluter 28 includes a pump 30 and connects to a diluent supply line 32 and a vehicle exhaust supply line 34. The diluent supply line 32 supplies a non-reactive zero gas and the vehicle exhaust supply line 34 supplies vehicle exhaust gas to be tested by the emission analysis test bench 12. The non-reactive zero gas is preferably nitrogen gas ($N_2$). A multi-component span gas supply line 36 supplies a blend of diluted samples of HC, $NO_X$, CO, and $CO_2$. A diluent flow controller 38 controls the flow rate of the non-reactive zero gas, a vehicle exhaust flow controller 40 controls the flow rate of the vehicle exhaust, and a span gas flow controller 42 controls the flow rate of the span gas. The diluent flow controller 38, the vehicle exhaust flow controller 40, and the span gas flow controller 42 are variable flow controllers and are preferably mass flow controllers. Those skilled in the art can appreciate that more than one span gas blend could be supplied and may contain other reactive gases or different span concentrations for calibrating the exhaust gas analyzers 14, 16, 18, and 20 over different ranges.

During operation, the pump 30 forces exhaust gas samples from a vehicle exhaust system, for example a vehicle tailpipe, from the vehicle exhaust supply line 34 to the diluter 28. The diluent supply line 32 supplies the non-reactive zero gas to the diluter 28, where the exhaust gas samples are diluted to levels suitable for testing. The diluted samples are directed through the supply manifold 26 to the exhaust gas analyzers 14, 16, 18, and 20 and the exhaust gas analyzer bypass line 22 for testing. The exhaust gas analyzers 14, 16, 18, and 20 perform simultaneous computerized analysis of the concentrations of HC, $NO_X$, CO, and $CO_2$ in the diluted samples.

To ensure the exhaust gas analyzers 14, 16, 18, and 20 perform accurate testing, the exhaust gas analyzers 14, 16, 18, and 20 are periodically calibrated. To calibrate the exhaust gas analyzers 14, 16, 18, and 20, the vehicle exhaust flow controller 40 is closed and the span gas is supplied by the multi-component span gas supply line 36. The span gas preferably includes all of the gases tested by the exhaust gas analyzers 14, 16, 18, and 20 in concentrations equal to the maximum test range for each respective exhaust gas analyzer 14, 16, 18, or 20. The exhaust gas analyzers 14, 16, 18, and 20 are first zeroed by simultaneously supplying only the non-reactive zero gas to the exhaust gas analyzers 14, 16, 18, and 20. The high points of the ranges of the exhaust gas analyzers 14, 16, 18, and 20 are determined by supplying only the span gas to the exhaust gas analyzers 14, 16, 18, and 20. A sample mixture is created by diluting the span gas with the non-reactive zero gas. The sample mixture produces intermediate readings of the exhaust gas analyzers 14, 16, 18, and 20. The diluent flow controller 38 continuously varies the concentration of the non-reactive zero gas in the sample mixture as a function of time so that an ideally infinite number of intermediate values can be recorded by the exhaust gas analyzers 14, 16, 18, and 20. The span gas flow controller 42 may also continuously vary the concentration of the span gas in the sample mixture as a function of time to achieve a broader range of intermediate values. A mixing chamber 44 improves the stability of the sample mixture.

A controller 45 receives signals 46 from the exhaust gas analyzers 14, 16, 18, and 20, which include the recorded intermediate values of the sample mixture. The controller 45 determines a response function for each of the exhaust gas analyzers 14, 16, 18, and 20 based on the recorded data. While a single controller 45 is shown in FIG. 1, those skilled in the art can appreciate that the exhaust gas analyzers 14, 16, 18, and 20 may have independent controllers that are capable of communicating over a network and through wired or wireless communication methods. The controller 45 may also be part of a computer used to monitor the emission analysis test bench 12.

While the diluent flow controller 38 and the span gas flow controller 42 continuously vary the concentrations of the non-reactive zero gas and the span gas in the sample mixture, the exhaust gas analyzers 14, 16, 18, and 20 record the concentrations of HC, $NO_X$, CO, and $CO_2$ in the sample mixture. However, the exact concentrations of the HC, $NO_X$, CO, and $CO_2$ in the sample mixture are determined by the FID analyzer 14, which has a predetermined response to HC. The FID analyzer 14 gives an accurate linear output. Those skilled in the art can appreciate that another previously calibrated exhaust gas analyzer or one with an accurate predetermined response other than the FID analyzer 14 could be used to determine the specific concentrations of the gases in the sample mixture. The controller 45 determines the exact concentrations of HC, $NO_X$, CO, $CO_2$, and $N_2$ in the sample mixture based on readings obtained by the FID analyzer 14. The controller 45 compares the exact concentrations of HC, $NO_X$, CO, $CO_2$, and $N_2$ to the response functions of the exhaust gas analyzers 14, 16, 18, and 20 to determine proper functioning of the exhaust gas analyzers 14, 16, 18, and 20. If necessary, the controller 45 takes corrective action to adjust the responsive properties of the exhaust gas analyzers 14, 16, 18, and 20.

In addition to calibrating the exhaust gas analyzers 14, 16, 18, and 20, the method of the present invention can diagnose a fault in the operation of the exhaust gas analyzers 14, 16, 18, and 20 on a regular basis. A calibrated exhaust gas analyzer 14, 16, 18, or 20 that continues to operate improperly may be defective.

Figure 2:
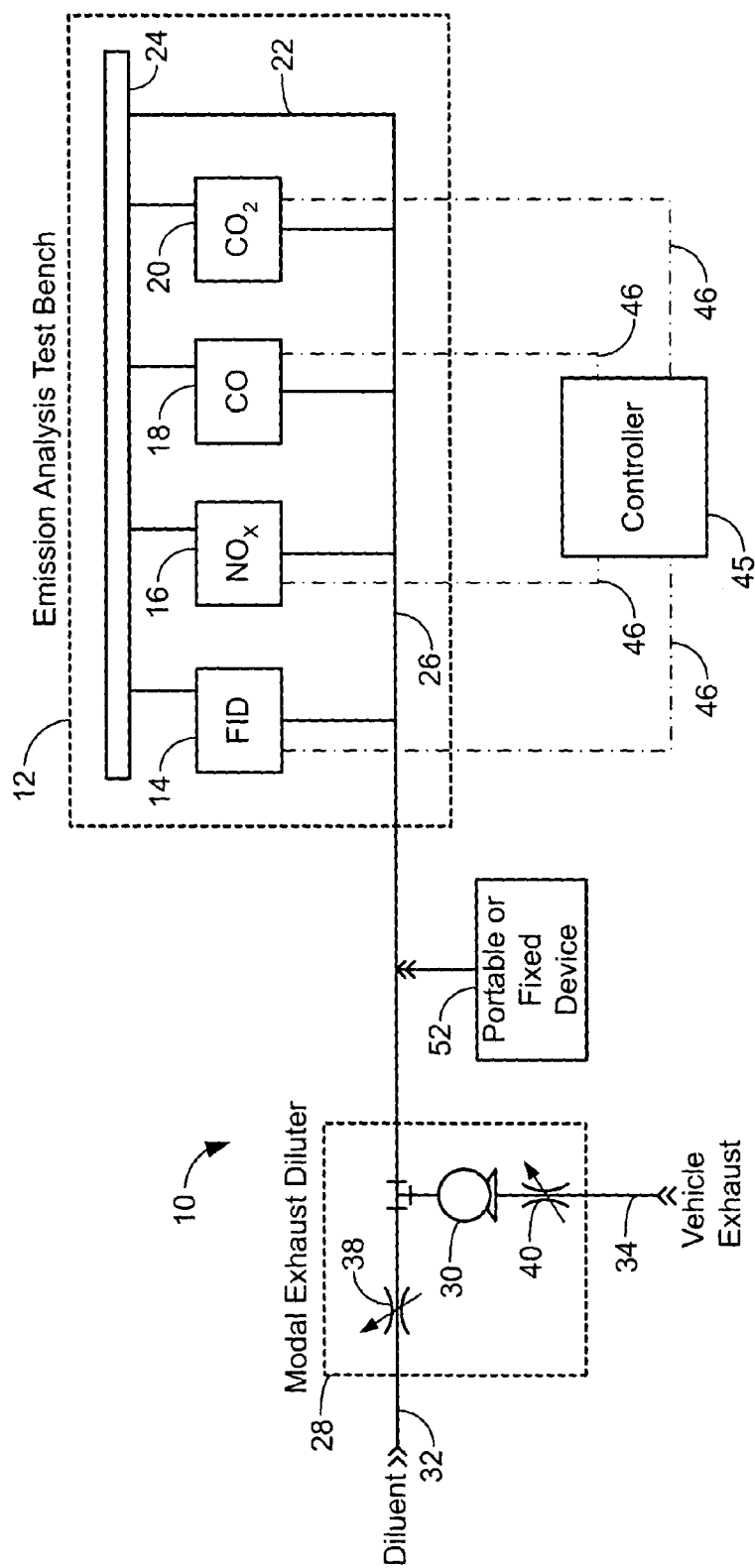
FIG. 2 is a schematic of an emission analysis test bench including a self-contained divider for exhaust gas analyzer calibration.

Referring now to FIG. 2, the multi-component span gas supply line 36, the span gas flow controller 42, and the mixing chamber 44 are incorporated into a self-contained divider 52 for exhaust gas analyzer calibration. The self-contained divider 52 preferably includes an independent diluent supply line and an independent diluent flow controller. The self-contained divider 52 eliminates the need to incorporate a multi-component span gas supply line into every gas flow system for an emission analysis test bench. The self-contained divider 52 can also be permanently added into an existing gas flow system as it contains all of the required elements for exhaust gas analyzer calibration. When the self-contained divider 52 is added between the supply manifold 26 and the vehicle exhaust supply line 34, the diluent flow controller 38 and the vehicle exhaust flow controller 40 are closed to calibrate the exhaust gas analyzers 14, 16, 18, and 20.

Figure 3:
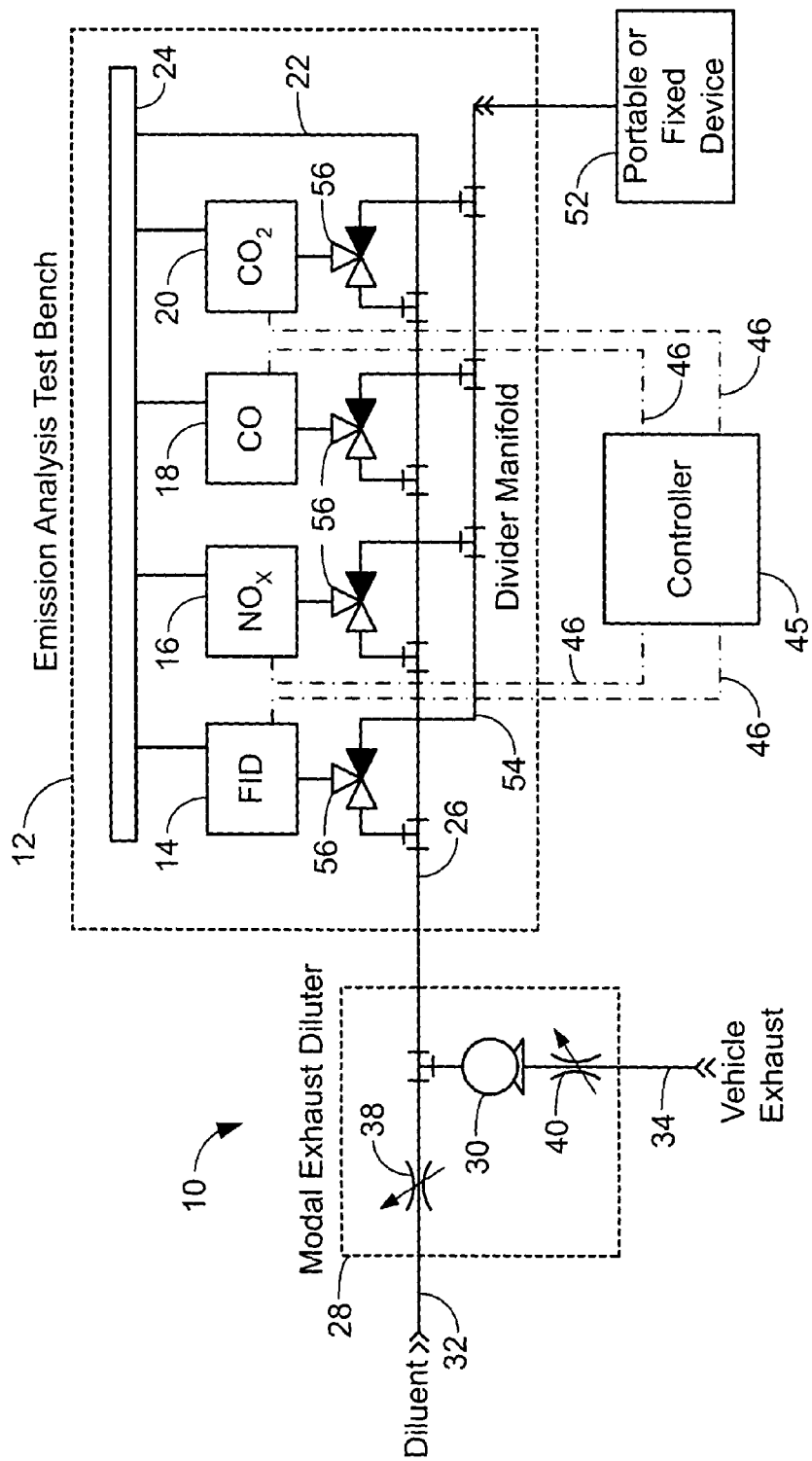
FIG. 3 is a schematic of an emission analysis test bench including a divider manifold and the self-contained divider.

Referring now to FIG. 3, the emission analysis test bench 12 includes a divider manifold 54. Divider manifolds are common on emission analysis test benches that incorporate separate span gases for each exhaust gas analyzer and/or each exhaust gas analyzer range. Valves 56 direct a gas flow from either the supply manifold 26 or the divider manifold 54 to the exhaust gas analyzers 14, 16, 18, and 20. The valves are preferably three-way solenoid vales that include a normally open port, a normally closed port, and a common port. The self-contained divider 52 is shown interfaced with the divider manifold 54. Interfacing the self-contained divider 52 with an emission analysis test bench 12 that includes a divider manifold eliminates the need to dismantle the divider manifold, tap into an existing supply manifold, or install a new supply manifold to perform exhaust gas analyzer calibration.

Figure 4:
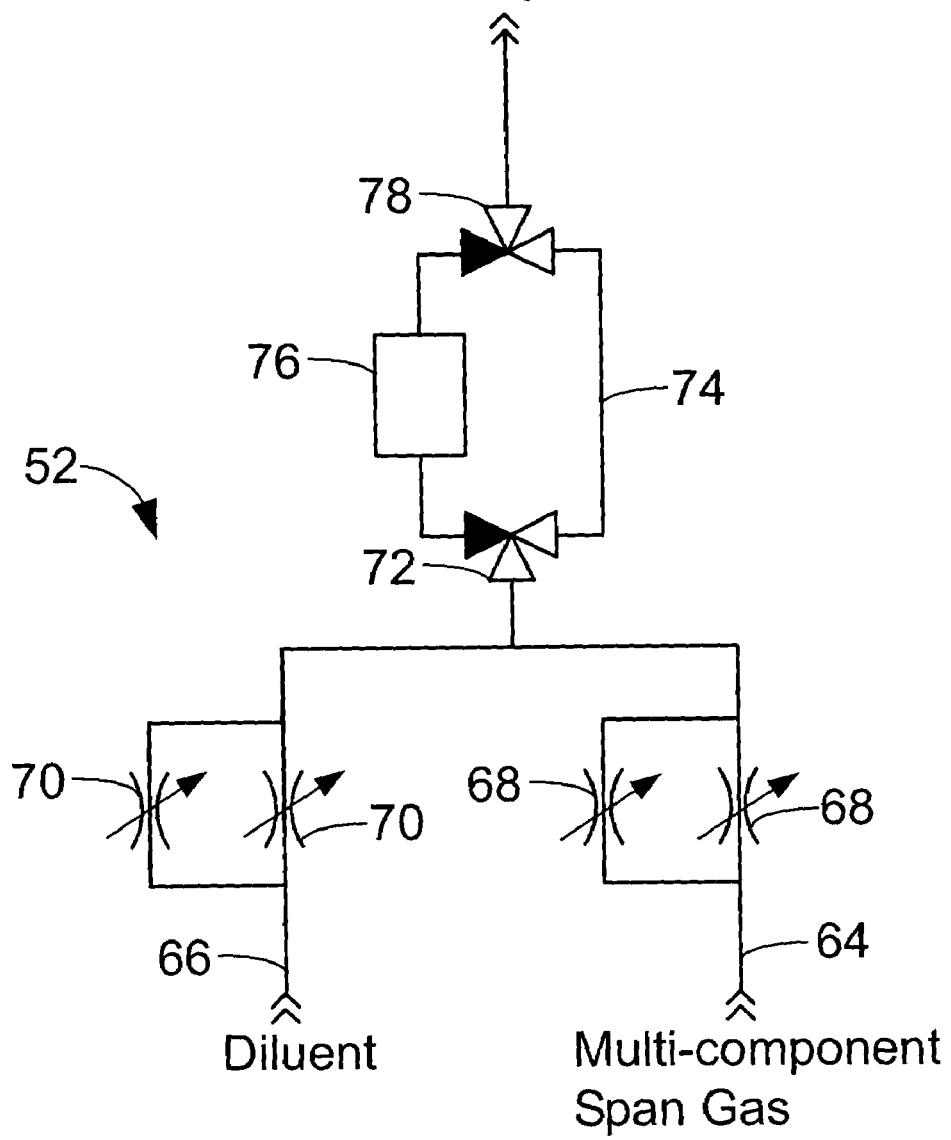
FIG. 4 is a schematic of an exemplary self-contained divider.

Referring now to FIG. 4, an exemplary self-contained divider 52 includes a portable span gas supply line 64 to supply the span gas. A portable diluent supply line 66 supplies the non-reactive zero gas. One or more portable span gas flow controllers 68 control a concentration of the span gas in a sample mixture of the span gas and the non-reactive zero gas. One or more portable diluent flow controllers 70 control a concentration of the non-reactive zero gas in the sample mixture. Additional flow controllers generate more precise concentrations of the gases. A first valve 72 directs the sample mixture from a bypass line 74 to a portable mixing chamber 76 that improves the stability of the sample mixture. A second valve 78 directs the sample mixture from the portable mixing chamber 76 or the bypass line 74 to the emission analysis test bench 12.

Continuous blending of the span gas and the non-reactive zero gas as a function of time is an improvement over prior methods of exhaust gas analyzer calibration. The continuous blending is preferably performed as a linear function of time, but other functions of time could also be used. The continuous blending provides an ideally limitless number of data points to more accurately describe the response functions of the exhaust gas analyzers 14, 16, 18, and 20. The present invention also eliminates the need to perform calibration over different ranges of the exhaust gas analyzers 14, 16, 18, and 20. All of the ranges can be tested at one time, significantly reducing the time required for the calibration. Also, the long stabilization periods of discrete division dividers are avoided. The continuous blending is preferably performed slow enough so that a time delay of the exhaust gas analyzers 14, 16, 18, and 20 and/or the mixing chamber 44 does not result in errors and the readings are accurate. While the blending is continuously performed, a normal exponential decay to a final stabilized reading will still occur. However, compensation can be provided for the time delay.

Reducing the calibration time of an exhaust gas analyzer minimizes adverse effects caused by exhaust gas analyzer drifting. Hysteresis in the exhaust gas analyzers 14, 16, 18, and 20 can also be avoided through continuous blending. The sample mixture of span gas and non-reactive zero gas can first be blended from a high concentration of span gas to a low concentration. Then, the sample mixture can be blended from a low concentration of span gas to a high concentration. Adverse effects due to hysteresis can be eliminated by generating the response functions of the exhaust gas analyzers 14, 16, 18, and 20 based on a composite of the two sets of data.

Continuous blending for calibration according to the present invention is more closely related to actual engine exhaust gas testing than prior methods that implement discrete divisions of span gas and zero gas. The composition of engine exhaust gas dynamically changes during engine exhaust gas testing, and discrete division methods require long stabilization times between readings. Continuous blending avoids long stabilization times while providing an increased number of calibration points to more accurately describe the response of an engine exhaust gas analyzer.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification, and the following claims.

The invention claimed is:

1. A method for calibrating a plurality of gas analyzers, comprising:
   providing a first gas analyzer that measures a first concentration of a first gas;
   providing a second gas analyzer that measures a second concentration of a second gas;
   providing a span gas that includes a mixture of said first gas and said second gas;
   supplying a calibration mixture to both said first gas analyzer and said second gas analyzer, wherein said calibration mixture includes said span gas and a non-reactive zero gas; and
   varying at least one of a third concentration of said non-reactive zero gas and a fourth concentration of said span gas in said calibration mixture as a function of time, wherein at least one of said third concentration and said fourth concentration is varied as a linear function of time.

2. The method of claim 1 wherein said first gas analyzer generates a first set of readings of said first concentration and said second gas analyzer generates a second set of readings of said second concentration.

3. The method of claim 2 wherein a controller generates a first response function of said first gas analyzer based on said first set of readings and said controller generates a second response function of said second gas analyzer based on said second set of readings.

4. The method of claim 3 wherein said first gas analyzer has a predetermined response to said first gas and said controller determines an exact concentration of said second gas in said calibration mixture based on said first set of readings.

5. The method of claim 4 wherein said predetermined response is determined through precalibration of said first gas analyzer.

6. The method of claim 4 wherein said predetermined response is linear.

7. The method of claim 4 wherein said first gas analyzer is a flame ionization detector that measures HC.

8. The method of claim 4 wherein said controller calibrates said second gas analyzer based on said second response function and said exact concentration.

9. The method of claim 4 wherein said controller diagnoses a defect in said second gas analyzer based on said second response function and said exact concentration.

10. The method of claim 2 further comprising:
mathematically compensating for a time delay in acquiring at least one reading in said first set of readings and said second set of readings.

11. The method of claim 1 wherein said first gas and said second gas are selected from the group consisting of hydrocarbons (HC), nitrogen oxides ($NO_x$), carbon monoxide (CO), and carbon dioxide ($CO_2$).

12. The method of claim 1 wherein said calibration mixture is blended in a mixing chamber.

13. The method of claim 1 wherein a portable device that includes said first gas, said second gas, said zero gas, and a mixing chamber supplies said calibration mixture.

14. A method for calibrating a plurality of gas analyzers, comprising:
providing a first gas analyzer that measures a first concentration of a first gas and that generates a first set of readings of said first concentration;
providing a second gas analyzer that measures a second concentration of a second gas and that generates a second set of readings of said second concentration;
providing a span gas that includes a mixture of said first gas and said second gas;
supplying a calibration mixture to both said first gas analyzer and said second gas analyzer, wherein said calibration mixture includes said span gas and a non-reactive zero gas;
varying at least one of a third concentration of said non-reactive zero gas and a fourth concentration of said span gas in said calibration mixture as a function of time;
increasing said third concentration as a function of time to generate a first decreasing set of readings of said first concentration and a second decreasing set of readings of said second concentration; and
decreasing said third concentration as a function of time to generate a first increasing set of readings of said first concentration and a second increasing set of readings of said second concentration.

15. The method of claim 14 wherein a controller generates a first response function of said first gas analyzer based on a composite of said first decreasing set of readings and said first increasing set of readings, and said controller generates a second response function of said second gas analyzer based on a composite of said second decreasing set of readings and said second increasing set of readings.

16. A method for calibrating a plurality of gas analyzers, comprising:
providing a span gas supply that includes a mixture of a first gas and a second gas;
providing a diluent gas supply that includes a non-reactive zero gas;
providing at least one diluent flow controller that controls a first concentration of said non-reactive zero gas in a calibration mixture of said first gas, said second gas, and said non-reactive zero gas; and
providing at least one span gas flow controller that controls a second concentration of said mixture in said calibration mixture,
wherein at least one of said first concentration and said second concentration is varied in said calibration mixture as a function of time and wherein said at least one of said first concentration and said second concentration is varied at a rate that is slower than a decay rate of said calibration mixture.

17. A method for calibrating a plurality of gas analyzers, comprising:
providing a span gas supply that includes a mixture of a first gas and a second gas;
providing a diluent gas supply that includes a non-reactive zero gas;
providing at least one diluent flow controller that controls a first concentration of said non-reactive zero gas in a calibration mixture of said first gas, said second gas, and said non-reactive zero gas; and
providing at least one span gas flow controller that controls a second concentration of said mixture in said calibration mixture,
wherein at least one of said first concentration and said second concentration is varied in said calibration mixture as a function of time, wherein said function of time is linear.

18. The method of claim 17 wherein said calibration mixture is supplied to an emission analysis test bench.

19. The method of claim 17 further comprising:
a mixing chamber that blends said calibration mixture;
a first valve that directs said calibration mixture to an input of said mixing chamber; and
a second valve that directs said calibration mixture from an output of said mixing chamber to an emission analysis test bench.

20. A method for calibrating a plurality of gas analyzers, comprising:
providing a first gas analyzer that measures a first concentration of a first gas and that generates a first set of readings of said first concentration;
providing a second gas analyzer that measures a second concentration of a second gas and that generates a second set of readings of said second concentration;
providing a span gas that includes a mixture of said first gas and said second gas;
supplying a calibration mixture to both said first gas analyzer and said second gas analyzer, wherein said calibration mixture includes said span gas and a non-reactive zero gas;
varying at least one of a third concentration of said non-reactive zero gas and a fourth concentration of said span gas in said calibration mixture as a function of time; and
mathematically compensating for a time delay in acquiring at least one reading in said first set of readings and said second set of readings.

* * * * *